US006512153B1

(12) United States Patent
Cappellazzo et al.

(10) Patent No.: US 6,512,153 B1
(45) Date of Patent: Jan. 28, 2003

(54) PROCESS FOR THE ALKYLATION OF AROMATIC COMPOUNDS

(75) Inventors: Oscar Cappellazzo, Alghero (IT); Gianni Girotti, Novara (IT); Massimiliano Pollastri, Bologna (IT); Sergio Lombardini, Milan (IT); Domenico Piccininno, Alghero (IT)

(73) Assignee: Enichem S.p.A., San Donato Milanese (IT)

( * ) Notice: Subject to any disclaimer, the term of this patent is extended or adjusted under 35 U.S.C. 154(b) by 0 days.

(21) Appl. No.: 09/612,256

(22) Filed: Jul. 7, 2000

(30) Foreign Application Priority Data

Jul. 13, 1999 (IT) .......................... MI99A1531

(51) Int. Cl.⁷ ................................. C07C 2/66
(52) U.S. Cl. .................. 585/467; 585/446; 585/448; 585/450; 585/323
(58) Field of Search ............... 585/467, 446, 585/450, 448, 323

(56) References Cited

U.S. PATENT DOCUMENTS

| 5,015,768 A | 5/1991 | Araki et al. ............... 568/798 |
| 5,030,786 A | * 7/1991 | Shamshoum et al. ....... 585/467 |
| 5,811,612 A | 9/1998 | Girotti et al. ............... 585/467 |
| 6,084,143 A | 7/2000 | Girotti et al. ............... 585/467 |

FOREIGN PATENT DOCUMENTS

| EP | 0 538 518 | 4/1993 |
| FR | 2 662 438 | 11/1991 |

\* cited by examiner

*Primary Examiner*—Walter D. Griffin
(74) *Attorney, Agent, or Firm*—Oblon, Spivak, McClelland, Maier & Neustadt, P.C.

(57) ABSTRACT

Process for the alkylation of aromatic compounds by the reaction of the aromatic compound of interest with isopropanol, alone or mixed with propylene, wherein the reaction is carried out in the presence of a catalytic composition based on zeolite, under mixed gas-liquid phase conditions or under completely liquid phase conditions, at such temperature and pressures that the concentration of water in the reaction liquid phase is not higher than 8,000 ppm w/w, regardless of the total water content present in the reaction mixture.

47 Claims, 11 Drawing Sheets

PROCESS FOR THE ALKYLATION OF AROMATIC COMPOUNDS

BACKGROUND OF THE INVENTION

1. Field of the Invention

The present invention relates to a process for the alkylation of aromatic compounds by the reaction of the aromatic compound of interest with isopropanol (IPA), alone or mixed with propylene, said reaction taking place in the presence of a catalytic composition based on zeolite and characterized in that the reaction mixture is present in mixed gas-liquid phase or in completely liquid phase under such temperature and pressure conditions that the concentration of water present in the liquid phase does not exceed 8,000 ppm w/w.

In particular, the present invention relates to a process for the alkylation of aromatic compounds in which said alkylation reaction, carried out with isopropanol or mixtures of isopropanol with propylene, is effected in the presence of a catalytic system comprising or consisting of a beta zeolite.

Even more specifically, the present invention relates to a process for the alkylation of benzene with isopropylic alcohol, and optionally propylene, to give cumene in the presence of a catalyst comprising or consisting of beta zeolite, said process being characterized in that the reaction mixture is present in mixed gas-liquid phase or in completely liquid phase under such temperature and pressure conditions that the concentration of water present in the liquid phase of said reaction mixture does not exceed 8,000 ppm w/w, and is preferably lower than or equal to 7,000 ppm w/w.

The above limit is regardless of the total water content in the reaction mixture stoichiometrically corresponding to the total quantity of isopropanol (IPA) in the feeding to the reaction section.

The process is characterized by the total absence of negative effects on the performance and duration of the catalyst due to the presence of high quantities of water in the reaction mixture.

The invention also relates to the process for preparing phenol in which the first preparation step of cumene is effected by the alkylation of benzene according to what is specified above.

2. Description of the Background

Cumene is an important precursor for the production of phenol, which in turn is useful as an intermediate in the preparation of caprolactam from which nylon is produced.

The complete preparation process of phenol comprises the alkylation of benzene to cumene and the oxidation of cumene to the corresponding hydroperoxide which, by acid treatment, generates phenol and acetone.

With respect to the first alkylation step, catalysts based on phosphoric acid and infusorial earth in a fixed bed reactor or $AlCl_3$ in slurry, are still widely used in the petrochemical industry, for alkylating benzene with propylene.

These processes however create problems relating to environmental impact and safety: in fact, the use of these catalysts is particularly problematical due to corrosion, the by-production of toxic organic products and disposal of the exhausted catalysts.

In 1965 the preparation of cumene using X or Y zeolite was described for the first time (Minachev, Kr. M., et al, Neftekhimiya 5 (1965) 676). The use of zeolites with a faujasitic structure for the alkylation of benzene with light olefins, such as propylene, was subsequently described by Venuto et al. in J. Catal.5, (1966)81.

U.S. Pat. No. 4,292,457 describes the use of ZSM-5 type zeolites for alkylating benzene with propylene.

Excellent results, in terms of industrial application, have been obtained in the synthesis of cumene using zeolites with a beta type structure, as described in EP 432,814, and in particular using catalysts comprising beta zeolite as described in EP 687,500.

Once obtained, cumene is transformed into phenol by means of an oxidation step to cumylhydroperoxide, followed by an acid treatment step which causes breakage of the peroxide bond with the formation of phenol and acetone.

If, on the one hand, the simultaneous production of phenol and acetone in a single productive unit is certainly a positive aspect from an industrial point of view, on the other hand the existence of an unbalanced commercial demand for the two products can cause problems in running an industrial plant for the production of phenol.

The necessity is therefore strongly felt for finding a possible use for present and future excess quantities of acetone.

U.S. Pat. No. 5,017,729 describes a process for the production of phenol via cumene hydroperoxide characterized by the use of propylene, in the preparation step of cumene, either totally or partially deriving from the reduction with hydrogen of acetone (co-produced with phenol) and subsequent dehydration of isopropylic alcohol.

The high costs of the various steps for re-obtaining pure propylene—to be used in the alkylation step—starting from the acetone co-produced with phenol, are evident in this process.

In particular, in the process proposed by Mitsui for the production of propylene starting from acetone, it appears that the higher investment costs can be attributed to the dehydration section of isopropanol—obtained from acetone in the relative reduction section with hydrogen—to propylene.

It is known, in fact, that the dehydration step of isopropylic alcohol to propylene is necessary, for concrete industrial application, due to the impossibility of carrying out the alkylation of benzene directly with isopropylic alcohol as alkylating agent, when acid catalysts of the conventional type are used, as a result of the water released from IPA during the reaction, which has negative effects on the catalyst performance in terms of selectivity and, above all, duration of the catalyst itself.

Acid catalysts—both of the zeolitic and non-zeolitic type—are in fact negatively influenced by the presence of water which is developed when isopropylic alcohol is used as alkylating agent of benzene to give cumene.

In the case of a catalyst of the conventional type such as, for example, phosphoric acid supported on silica, widely used in the industrial synthesis of cumene, quantities of water higher than a few hundred ppm in the reaction mixture produce a significant chemical and mechanical disgregation of the catalyst together with a considerable lowering of catalytic performances in terms of yield to cumene.

In the case of catalysts based on zeolites, the negative effect due to the presence of water which causes a lowering of the overall yield to cumene, together with a more or less rapid deactivation of the catalyst itself, is known. All these negative effects are known and verified also with very low contents of water—present in the reaction—with respect to those caused by the use of isopropylic alcohol as alkylating agent of benzene to give cumene in a process applicable on an industrial scale.

The industrial applicability of an alkylation process of benzene with isopropylic alcohol cannot, in fact, fail to take into account certain parameters such as for example the molar ratio benzene/IPA in the feeding to the reaction section, which generally ranges from 4 to 8 with a corresponding concentration of water in the reaction equal to about 48,300 and 26,000 ppm w/w, when the alkylation is carried out with isopropanol alone, assuming the total conversion of the isopropanol itself.

The possibility of using IPA as alkylating agent of benzene to give cumene is described in Appl. Cat. A 95 (1993) 53–63, whose disclosure specifies that the relative process must be rigorously carried out in gas phase, and yet there is still a significant loss in the activity of the zeolitic catalyst used as the test proceeds.

U.S. Pat. No. 5,015,786 describes a production process of phenol via cumene in which part of the cumene derives from the alkylation of benzene, also effected with isopropylic alcohol obtained by the reduction of the acetone co-produced with phenol, together with cumene deriving from the alkylation of benzene with propylene.

The alkylation step of benzene with IPA is carried out in the presence of a catalyst of an acidic nature, selected from various materials: zeolites are indicated as preferred catalysts. It is interesting to note however that the above document provides no information as to the life of the catalyst and constancy of the performances in general due to the fact that the test with the longest duration lasts 200 hours (Example 5, column 15) which correspond, under the conditions specified, to a productivity not higher than about 100 Kg of cumene/Kg of catalyst.

The avoid the problems mentioned above, the use of particular hydrophobic zeolites has been proposed, such as ZSM-5 zeolite with a high silica/alumina ratio or dealuminated H-mordenite and Y zeolite.

For example, in U.S. Pat. No. 5,160,497 a dealuminated Y zeolite is used, with a molar ratio $SiO_2/Al_2O_3$ ranging from 8 to 70, for the alkylation of benzene with propylene and isopropanol.

SUMMARY OF THE INVENTION

We have now found that it is possible to obtain cumene by the alkylation of benzene with isopropylic alcohol, or a mixture of IPA and propylene as alkylating agent, by means of a process which provides better performances and above all catalyst duration, even in the presence of large quantities of water, using a zeolitic catalyst and operating under certain pressure and temperature conditions.

An object of the present invention, in fact, relates to a process for the alkylation of aromatic compounds in which the alkylation reaction is carried out with isopropanol, or mixtures of isopropanol with propylene and under such conditions that the quantity of water in liquid phase does not exceed 8,000 ppm w/w.

DETAILED DESCRIPTION OF THE INVENTION

Figure 1:
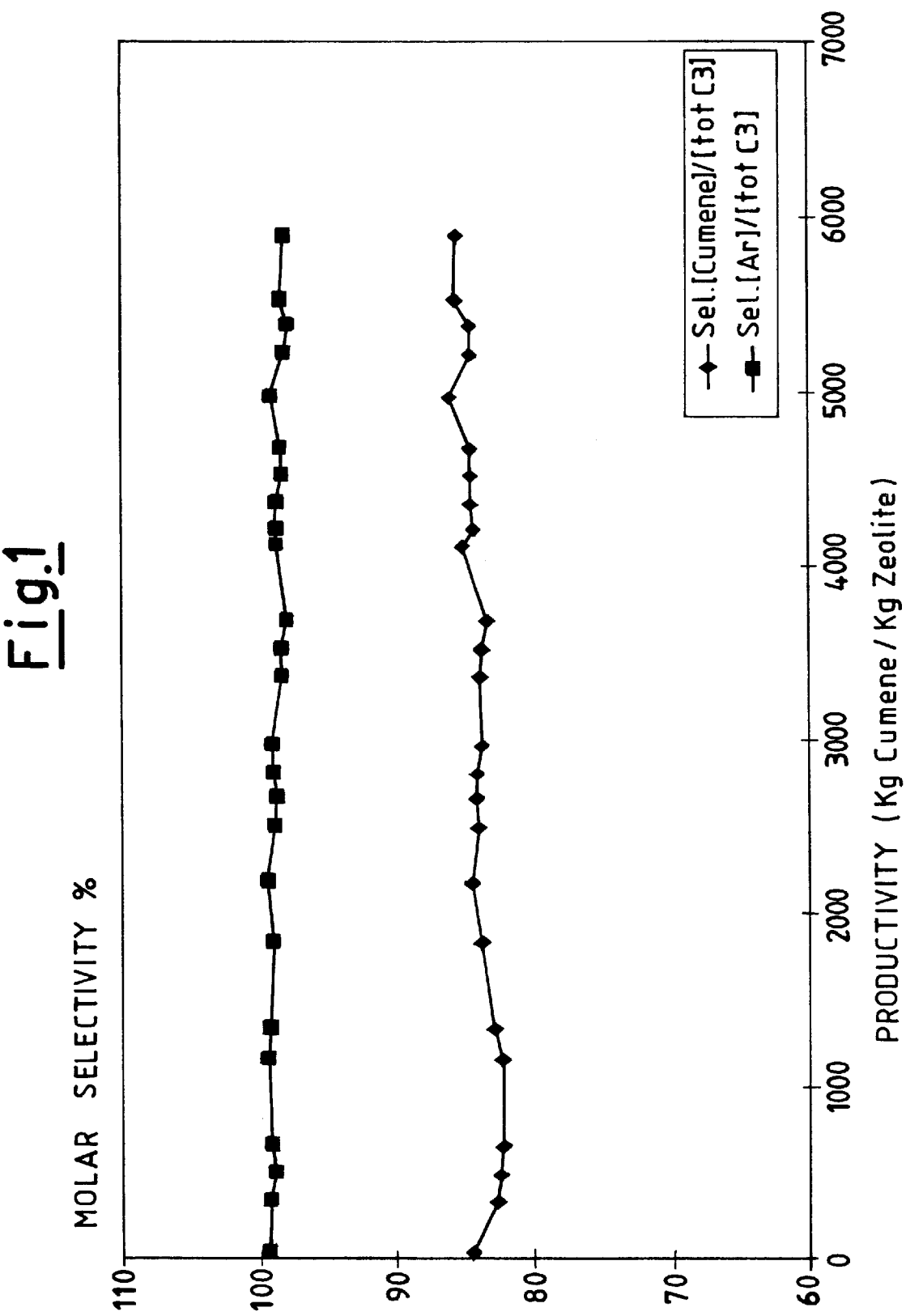
FIGS. 1 through 8 are graphs showing molar selectivity in relation to productivity.

More specifically, the above reaction is carried out in the presence of a zeolitic catalyst, by controlling the temperature and pressure conditions: the zeolite is selected from those of the "large pore" type and, in particular from beta, Y, ZSM-12 and mordenite.

In particular, an object of the present invention relates to a process for the alkylation of benzene, in which the alkylation reaction is carried out with isopropylic alcohol, or a mixture of isopropanol and propylene, to give cumene and water, conducted in the presence of a catalyst comprising or consisting of zeolite, said process being effected under such temperature and pressure conditions that the concentration of water present in the liquid phase is never higher than 8,000 ppm w/w, and is preferably equal to or lower than 7,000 ppm w/w; these conditions approximately correspond to a system in which the present phase can be mixed (liquid and gas), or entirely liquid.

The process according to the present invention can be carried out at any molar ratio between benzene and isopropylic alcohol in the feeding to the reaction section and consequently regardless of the total quantity of water developed during the reaction.

When operating in completely liquid phase, i.e. under temperature and pressure conditions corresponding to complete liquid phase of the overall reaction mixture, it is advisable to recycle the reaction effluent to keep the water concentration within the above limits, unless the content tent of isopropanol in the feed does not already stoichiometrically correspond to said limit.

Catalysts comprising or consisting of beta zeolite are those which seem to guarantee the best results of the process according to the present invention.

The beta zeolite used as catalyst of the process according to the present invention may be that described in U.S. Pat. No. 3,308,069, and is a porous crystalline material having the composition

$$[(x/n)M(1\pm0.1-x)TEA]AlO_2.ySiO_2.wH_2O$$

wherein n is the oxidation state of M, x is less than 1, y ranges from 5 to 100, w is from 0 to 4, M is a metal selected from those of groups IA, IIA, IIIA of the Periodic System or from transition metals and TEA is tetraethylammonium.

A preferred aspect of the present invention is that the beta zeolite is in acidic form i.e. in the form in which the H$^+$ion has partially or totally substituted the metal cations initially present.

This substitution is effected in accordance with the known methods by means of an exchange with ammonium ions, washing and subsequent calcination.

The beta zeolite can also be mixed with suitable binding agents, such as for example, oxides of silicon, aluminum, zirconium, magnesium, in a relative quantity ranging from 5:95 to 95:5.

A particularly preferred aspect of the present invention is to use catalytic compositions comprising beta zeolite described in EP 687,500 and EP 847,802, i.e. catalytic compositions consisting of beta zeolite and an inorganic ligand characterized by an extra-zeolite porosity consisting, for a fraction of at least 25%, of pores with a radius higher than 100 Å and, in the case of EP 847,802, also characterized by a total extra-zeolitic pore volume greater than or equal to 0.80 ml/g.

According to a preferred aspect of the present invention, the process is carried out at a reaction temperature ranging from 170° C. to 230° C., at a reaction pressure ranging from 10 to 50 bars under mixed phase conditions using isopropanol or mixtures of isopropanol and propylene indifferently as alkylating agent, together with a WHSV ranging from 10 h$^{-1}$ to 1 h$^{-1}$.

When the reaction is carried out under mixed phase conditions, the concentration of the water, which is formed as reaction by-product, in the liquid phase should not exceed, as already specified, 8,000 ppm, and is even more preferably present in concentrations lower than or equal to 7,000 ppm.

Experts in the field are able to define a priori—starting from the molar ratio [benzene]/[IPA] and [propylene]/[IPA] when propylene is also fed to the reaction section together with IPA—temperature and pressure conditions which respect the limit relating to the concentration of water present in the liquid phase equal to about 8,000 ppm w/w and preferably less than or equal to 7,000 ppm w/w, regardless of the total quantity of water present in the reaction mixture and consequently regardless of the quantity of isopropylic alcohol fed to the reaction section.

When the alkylation reaction of benzene with isopropanol or with mixtures of IPA and propylene is carried out in completely liquid phase, excellent results are equally obtained if the concentration of water in the reaction mixture does not exceed 8,000 ppm w/w and preferably remains equal to or lower than 7,000 ppm w/w, regardless of the total quantity of IPA fed to the reaction section.

In the process claimed herein, the molar ratio between benzene and isopropanol preferably varies from 3 to 10, even more preferably from 4 to 8.

When propylene is also additionally used as alkylating agent together with isopropanol, the molar ratio between benzene and alkylating agent isopropanol plus propylene varies from 3 to 10, more preferably from 4 to 8, and the molar ratio between isopropanol and propylene varies from 10 to 0.01 and even more preferably from 5 to 0.1.

The alkylation of benzene with isopropanol can be carried out in continuous, semi-continuous or batchwise.

When the process is carried out in continuous, it is also possible to use a configuration of the reaction system which comprises the partial recycling of the effluent of the reaction section, after cooling and separation of the aqueous phase from the organic phase, to the reaction section itself.

The recycling ratio to the reaction section, i.e. the weight ratio between the quantity of effluent from the reaction section re-fed to the reaction section itself and the quantity of effluent from the reaction section collected instead as product is greater than or equal to 0.2 and preferably ranges from 1 to 100.

The running of the reaction section in the configuration with recycling of the reactor effluent described above is convenient when the reaction is carried out in completely liquid phase of the reaction mixture and for IPA contents in the feeding higher than those stoichiometrically corresponding to the concentration of water specified above.

The alkylation reaction of benzene with IPA or mixtures of IPA and propylene as alkylating agent, remains however exothermal and in order to maintain the temperature within a preferred range and reduce the by-production of aromatic polyalkylated products, the catalyst can be distributed in the reactor in various layers inside a fixed bed reactor.

A quench is effected between one layer and another with inert solvents and/or part of the benzene and/or part of the isopropylic alcohol or mixture of isopropylic alcohol/propylene as alkylating agent.

Operating conveniently, high benzene/alkylating agent ratios can be obtained on the single layer, without increasing the same overall ratio, which is an obvious advantage with respect to the selectivity to cumene and consequently the separation operations downstream of the reaction section.

The temperature control can be effected not only by means of quenching the reagents and/or inert products, but also by means of inter-cooling between the layers.

The alkylation reaction can be suitably carried out in two or more reactors in series, inter-cooled to control the temperature. The feeding of the isopropylic alcohol, optionally mixed with propylene, and/or benzene, can be suitably divided between the various reactors and reactor layers, i.e. the alkylating agent and/or benzene are added in more than one step.

Cumene is also produced in an integrated alkylation process in which the same reaction unit (consisting of several alkylation reactors) can be contemporaneously run under different conditions between the reactors.

It is possible, in fact, to have one or more reactors in which the alkylating agent, either totally or partially, consists of isopropanol and one or more reactors in which the alkylating agent is propylene alone, in which case the conditions may be those described in European patent applications 687,500 and 847,802.

An example is provided hereunder for illustrative purposes of a reaction carried out with isopropanol as alkylating agent, or IPA and propylene, as alkylating agent: this example obviously does not restrict the scope of the present invention.

The alkylation of benzene in the presence of isopropanol can be carried out in the configuration with recycling of the reaction effluent to the reaction unit itself under the conditions already described above.

The necessity of this configuration is subordinate to the concentration of water present in the catalytic zone, as it is possible, in fact, with the recycling, to obtain its reduction in the organic effluent by means of simple dilution.

If the reaction mixture is in mixed phase, it is possible to vary the concentration of water in the catalytic zone by operating, as mentioned, on the reaction conditions and consequently on the vapor fraction of the reagent stream: on decreasing the pressure and/or increasing the temperature, there is an increase in this vapor fraction with a consequent decrease in the water concentration in the liquid phase, as the latter is more volatile than the rest of the mixture components.

The configuration of the fractionation section, downstream of the reaction section, has an important role in correctly managing the water developed in the reaction section itself.

The effluent from the reaction section described above, in order to reduce the concentration of water present, is first cooled and then separated into two phases, an organic phase and an aqueous phase; the aqueous phase is flushed from the plant, whereas the organic phase is fed to the fractionation section or also, when necessary, to the reactor itself as recycled product, if this is included in the configuration with recycling.

Figure 9:
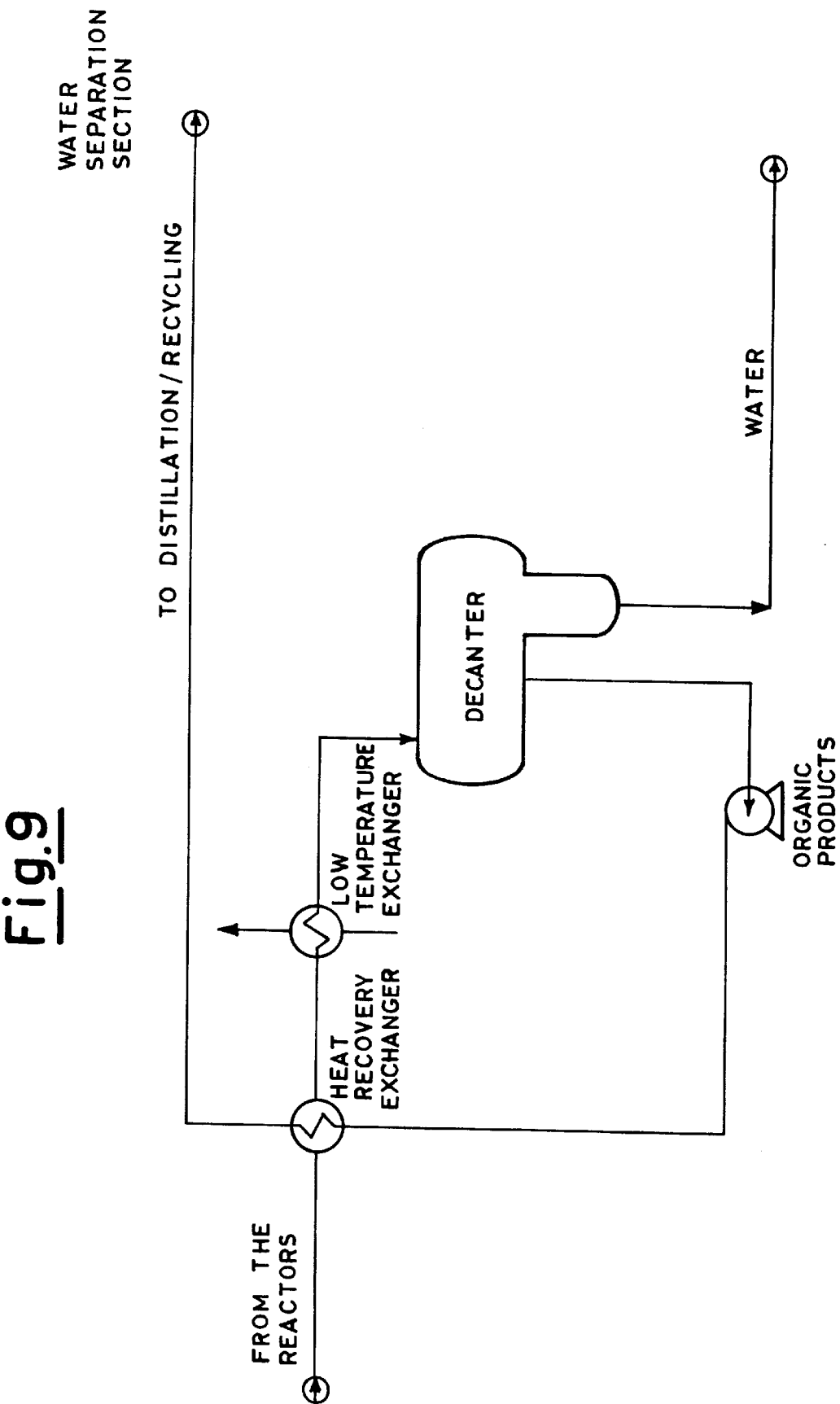
FIG. 9 shows a flow scheme relating to a cooling step of reaction effluent.

FIG. 9 indicates, for purely illustrative purposes of the invention, the simplified flow scheme relating to the cooling step of the reaction effluent described above, from which it can be assumed that the first cooling step is obtained by means of a thermal recovery with respect to the organic phase separated.

The process thus characterized allows great flexibility as far as the quantity of cumene deriving from the alkylation reaction section is concerned, obtained both with isopropanol as alkylating reagent and also with propylene.

This flexibility is also obtained thanks to the particular configuration of the fractionation section of the reaction products, as described hereunder.

Modifications to the fractionation section with respect to the known art of the cumene process via propylene concern the depropanating column for separating the propane normally present in the olefin in the alkylation charge.

The remaining columns of the typical fractionation section of a cumene plant via propylene, i.e. the debenzonating column, the cumene finishing column and the column for the separation of the diisopropylbenzenes to be sent to the transalkylation section, remain unaltered in the functioning procedure and consequently do not require further details.

Figure 10:
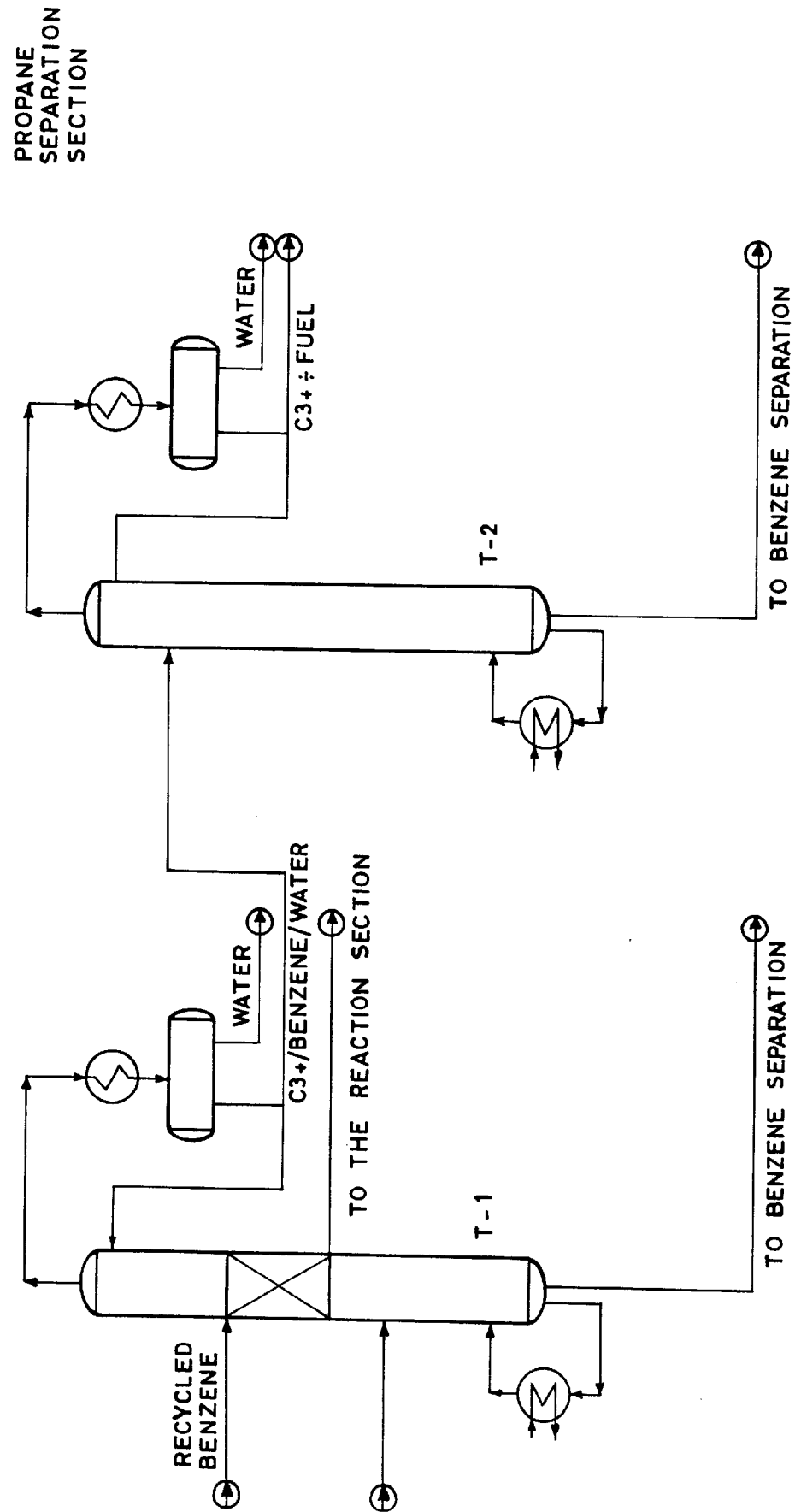
FIGS. 10 and 11 each show an embodiment containing two depropanating columns.

The asset modifications to the depropanating column(s) are indicated in FIG. 10 for purely illustrative purposes of the invention.

The first depropanating column T-1 is fed by the organic stream downstream of the cooling and separation unit, already qualitatively described and schematized in FIG. 9, and also receives a recycled stream of benzene in order to:

cool the vapors in the column, by reducing the thermal charge of the condenser;

heat the recycled benzene destined for the alkylation and transalkylation sections removed as lateral cut;

allow a deviation of part of the benzene present in the feeding to the column towards the lateral cut re-cycled to the reaction.

To limit the concentration of water recycled to the reaction sections in the lateral cut of the column T-1, it is therefore necessary to bring a high quantity of benzene into the product at the head of the column; with this asset of the column T-1, all the water in the feeding to this column, as well as not being separated from the organic phase on the plates, totally reaches the condenser at the head and is then separated in the reflux accumulator.

The stream at the head of column T-1, rich in benzene, feeds a second depropanating column T-2 which separates the benzene from the propane used in the reaction section as inert product and any possible water still present.

Two streams are produced from the bottom of columns T-1 and T-2, which are sent to the debenzenating column, already mentioned above, for the separation of the benzene.

The rest of the fractionation section, as already specified, has a configuration which is substantially analogous to a typical fractionation section of a cumene plant via propylene.

The case of a plant. for the production of cumene already existing and having two independent reaction sections, each with its own fractionation section, represents an additional possibility for applying the process according to the present patent application.

The alkylation of benzene with isopropanol or isopropanol and propylene as alkylating agent is carried out in one of the two existing reaction sections, whereas the alkylation of benzene with propylene alone as alkylating agent is carried out in the other.

In this particular case, there are already two depropanating columns, one for each of the two fractionation sections already existing, and the process therefore provides different procedures for running the two depropanating columns.

The cooling and separation section remains the same as that already illustrated in FIG. 9 and, also in this case, the basic operating procedures for the remaining columns forming part of the fractionation sections already existing, remain unaltered.

Figure 11:
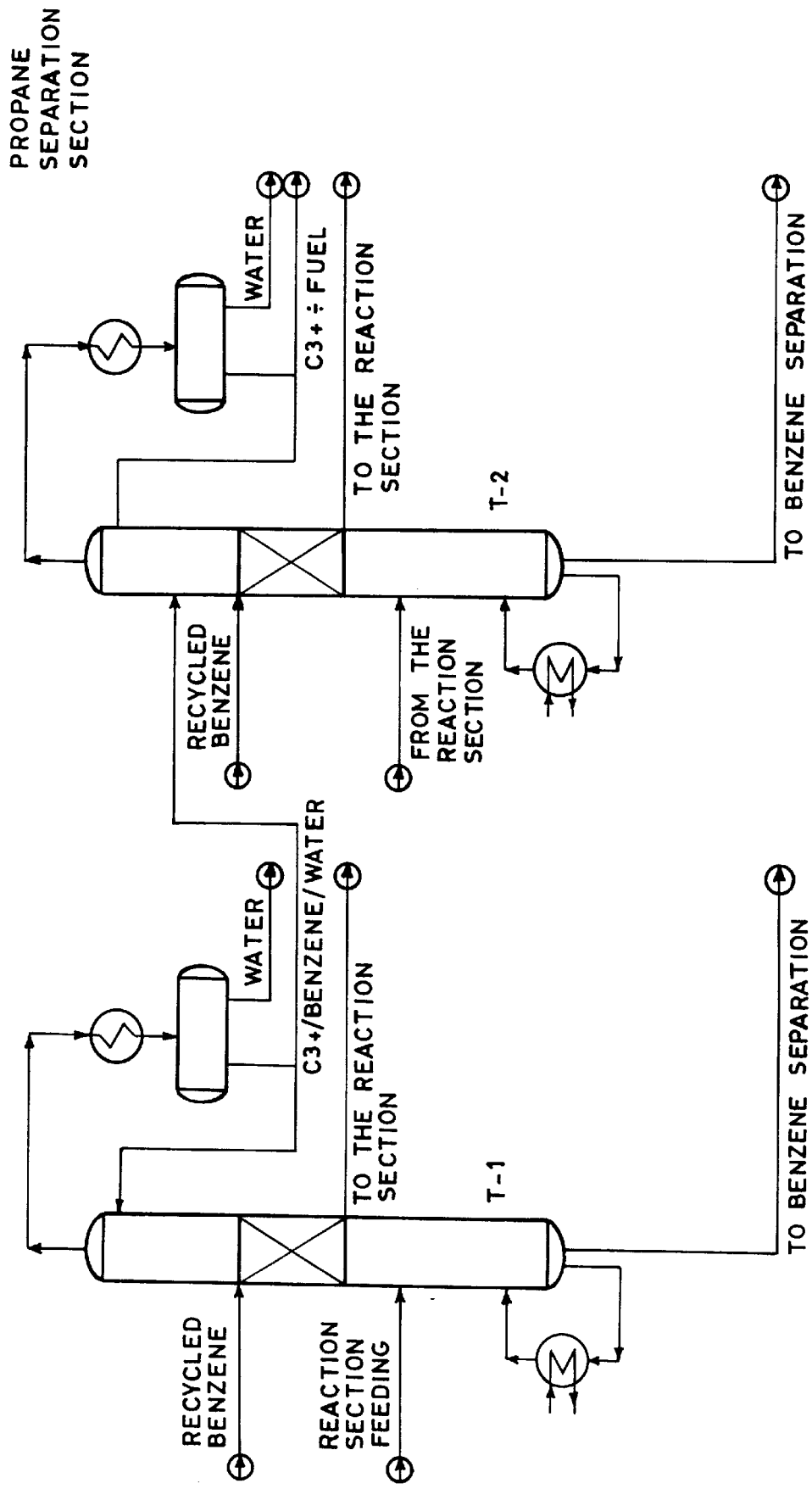

The operative asset of the two depropanating columns is schematized in FIG. 11 in which the differences in the operative asset, with respect to that illustrated in FIG. 10, can be noted. In particular, it can be observed that column T-1 is fed with effluents deriving from the reaction section in which the alkylation is carried out with isopropanol or isopropanol and propylene as alkylating agent, and column T-2 is fed with effluents deriving from the reaction section operating with propylene alone as alkylating agent. An object of the present invention also relates to a process for preparing phenol in which the formation of byproducts is controlled. This process comprises the following steps:

1) alkylation of benzene with isopropylic alcohol, and optionally propylene, to give cumene and water;
2) oxidation of the cumene thus obtained;
3) treatment of cumylhydroperoxide with acids to obtain a mixture of phenol and acetone;
4) hydrogenation of the acetone to isopropanol which is recycled to step 1.

In particular and according to a preferred embodiment:

1) the alkylation of benzene with isopropylic alcohol, and optionally propylene, to give cumene and water, is carried out in the presence of a catalyst based on beta zeolite and, preferably, with a catalyst prepared according to the procedure described in EP 687,500 and EP 847,802.

The pressure and temperature conditions with which the reaction is carried out are such as to guarantee that the concentration of water in the liquid phase is not higher than about 8,000 ppm, regardless of the total quantity of water present in the reaction system, and therefore of the quantity of isopropylic alcohol fed to the reaction section itself;

2) the cumene deriving from step 1 is oxidized with air to give cumyl hydroperoxide, which in turn is treated with an acid to give a mixture of phenol and acetone which is fractionated to separate the phenol from the acetone;
3) the acetone obtained in step 2 is partly or totally hydrogenated to isopropylic alcohol which is recycled to step 1.

According to a preferred aspect, at the end of the first step, after separating by fractionation the desired product, cumene, which passes to the subsequent oxidation step, the remaining fraction of polyisopropylbenzenes is used in a separate step for a transalkylation reaction with benzene to recover additional cumene.

The transalkylation reaction is carried out in the presence of beta zeolite or a catalyst based on beta zeolite, in particular prepared according to the procedure described in EP 687,500 and EP 847,802.

The temperature conditions for the transalkylation reaction are selected from 100° C. to 350° C., the pressure is selected from 10 to 50 atm and the WHSV ranges from 0.1 $h^{-1}$ to 200 $h^{-1}$, according to the procedure described in EP 687,500.

Consequently, in step (2), the cumene deriving from step (1), and optionally from the transalkylation step, is oxidized to cumyl hydroperoxide. The cumyl hydroperoxide is then transformed into phenol and acetone. In the last step, part of or all the acetone obtained as by-product in step (2) is hydrogenated to isopropylic alcohol which is re-fed to the initial step.

The hydrogenation reaction of acetone to isopropanol is already known and is carried out using catalysts based on Nickel Raney, nickel-copper, copper-chromium, copper-zinc or based on metals of the platinum group for example platinum, palladium, ruthenium, rhodium.

A catalyst based on Nickel Raney or copper-chromium is preferably used.

The conditions under which the hydrogenation reaction of acetone takes place are described, among others, in U.S. Pat. No. 5,015,786 or U.S. Pat. No. 5,017,729.

A remarkable aspect of the processes described herein and in particular of the alkylation step of benzene with isopropanol or mixtures of propylene and isopropanol, is the great flexibility in re-using the acetone co-produced with phenol, from which isopropylic alcohol is obtained by reduction with hydrogen. This flexibility is in fact obtained by the use of the catalyst (zeolitic) adopted in the process according to the invention, associated with the specific operating conditions of the reaction section which together guarantee the absence of performance reduction and rapid deactivation phenomena typical of solid acid catalysts due to the presence of water generated by the use of isopropylic alcohol as alkylating agent of benzene.

The following examples again provide a better illustration of the invention described herein, without however limiting its scope in any way:

EXAMPLE 1

An alkylation test of benzene with a mixture of isopropylic alcohol (IPA) and propylene (C3-) is carried out using an apparatus consisting of an AISI 316 fixed bed micro-pilot reactor, with an internal diameter of 1.3 cm, a total length of 150 cm, tanks for the benzene, isopropylic alcohol and propylene in the feeding, dosage pumps for the feeding of benzene and IPA, a mass flowmeter for dosing the propylene in liquid phase, an automatic system for the temperature and pressure control, for discharging the effluent from the reactor and for analyzing the feeding and product.

The reaction products, liquid and gaseous, are analyzed by means of gaschromatography using the following equipment:

(a) Carlo Erba GC 6000 gaschromatograph equipped with a MEGA SE54 column having an external diameter of 0.53 mm and a length of 25 m, FID detector and temperature program;

(b) HP 6890 gaschromatograph equipped with a PONA column having an external diameter of 0.2 mm and a length of 50 m, FID detector and temperature program;

(c) Carlo Erba 4200 gaschromatograph equipped with a Poro-pack-Q filled column having a diameter of 4 mm and a length of 2 m, TCD detector and temperature program.

The reaction conditions at which the test was carried out are as follows:

| | |
|---|---|
| Temperature at the inlet = | 180° C. |
| Pressure = | 14 barg |
| WHSV: | 20 h$^{-1}$ |
| [Benzene]/[C$_3$— + IPA] = | 7 moles/moles |
| [C$_3$—]/[IPA] = | 2.0 moles/moles |

The reaction conditions selected correspond to operating in mixed gas/liquid phase with a total concentration of water present equal to about 10,000 ppm and a concentration of water present in the liquid fraction equal to about 3,180 ppm.

The attribution of the physical state of the reagent mixture is effected both by comparison with the existing phase diagrams for the components and mixtures in question, and also by calculation, adopting the RKS state equation (Soave G. Chem. Eng. Sci 27, 1197, (1972)). The interaction parameters for this equation are obtained from regression of the experimental data in literature relating to liquid-vapor equilibrium and mutual solubilities of the hydrocarbon-water mixtures (C. C. Li, J. J. McKetta Jul. Chem. Eng. Data 8 271–275 (1963) and C. Tsonopoulos, G. M. Wilson ALCHE Journal 29, 990–999, (1983).

The reaction system to which the above equation is applied resembles, as far as the compositions are concerned, the system [benzene]/[propylene]=7 moles/moles and [benzene]/[water]=21.2 moles/moles.

A catalyst based on beta zeolite, prepared according to the procedure described in EP 687,500 and EP 847,802, is charged inside the reactor in a quantity corresponding to a catalytic bed height of 42.5 cm.

FIG. 1 shows the trend of the molar selectivity [Ar]/[totC$_3$] (Cumene+Diisopropylbenzenes+Triisopropylbenzenes with respect to the total propylene and IPA converted) and the molar selectivity [Cum.]/[totC$_3$] (Cumene with respect to the total propylene and IPA converted) during the test in relation to the productivity reached by the catalyst expressed in Kg Cumene/Kg zeolite.

For the whole duration of the test, there were no signs of deactivation of the catalyst such as, for example, a drop in the conversion of the isopropylic alcohol/propylene alkylating agent (quantitative for the whole duration of the test) or an increase in the fraction of polyalkylated products.

The selectivities during the whole test remained substantially unaltered with average values equal to about 84.0% for Sel.[Cum]/[totC$_3$] and about 98.8% for Sel. [Ar]/[totC$_3$].

It should be pointed out that the constancy of the two selectivity data during the whole test is extremely significant as it indicates a constant catalytic activity, also with respect to the transalkylation reaction of polyalkylated products, which, as is known to experts in the field, always takes place contemporaneously with the alkylation reaction.

The deactivation of the catalyst would, in fact, have been observed, even before a drop in the conversion of the reagents, by a decrease in the selectivity [Cum]/[totC$_3$] (also with the same [Ar]/[totC$_3$]selectivity) due to a reduction in the catalytic activity in the transalkylation reaction of polyalkylated products.

Example 2 (Comparative)

An alkylation test of benzene with a mixture of isopropylic alcohol and propylene is carried out using the same apparatus as that described in example 1. The catalyst used and the quantity charged into the reactor are the same as those specified in example 1. The reaction conditions during the test are the following:

| | |
|---|---|
| Temperature at the inlet = | 180° C. |
| Pressure = | 30 barg |
| WHSV: | 20 h$^{-1}$ |
| [Benzene]/[Propylene + IPA] = | 7 moles/moles |
| [Propylene]/[IPA] = | 2.0 moles/moles |

The reaction conditions selected correspond to operating in the presence of liquid phase alone instead of the mixed phase as described in the previous example, with a concentration of water in the liquid phase now equal to about 10,000 ppm total with respect to about 3,180 ppm of the previous example.

This attribution is effected, as already described in example 1, by assimilating the reaction system, as far as the compositions are concerned, to that already described in example 1.

Figure 2:
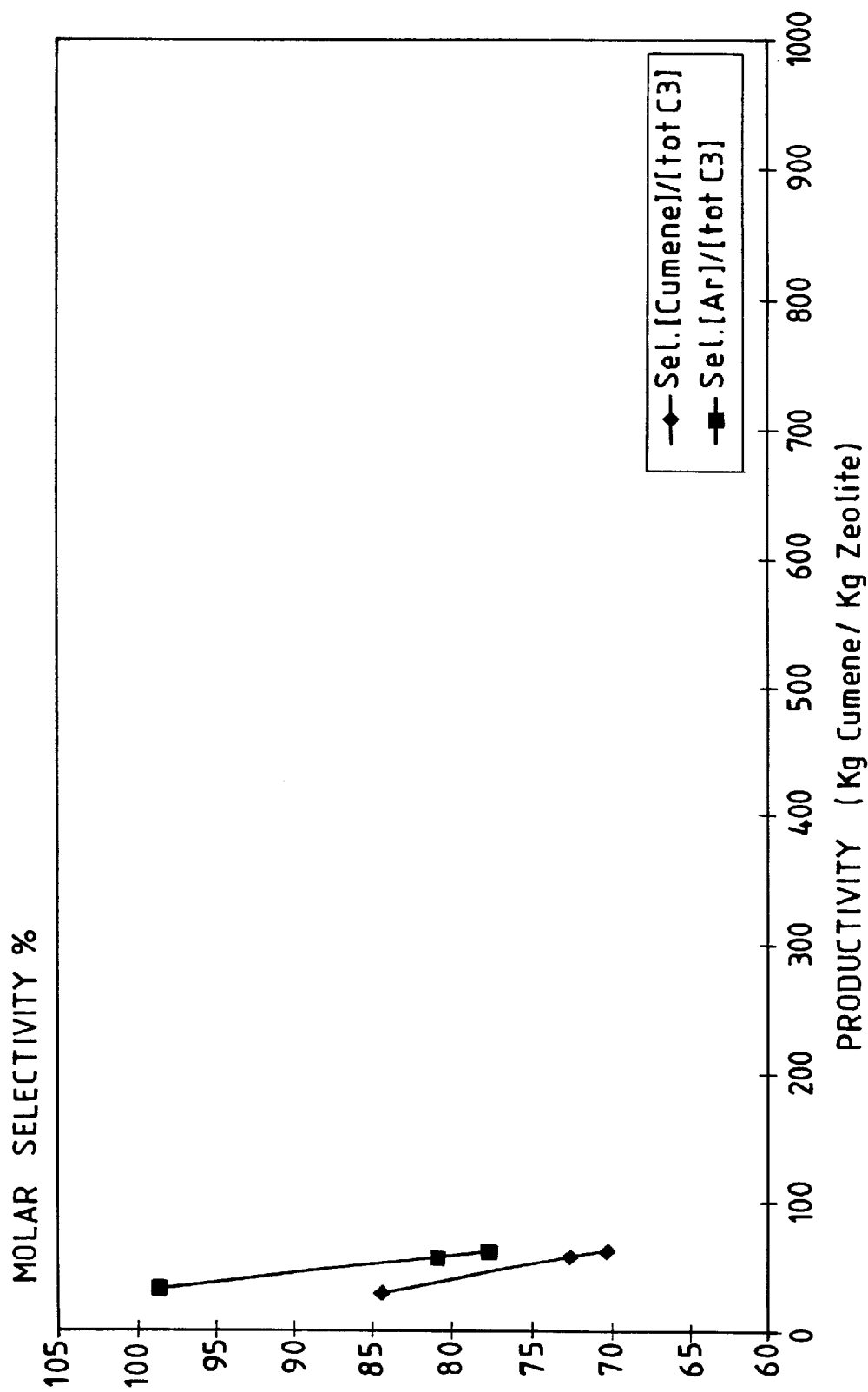

FIG. 2 shows the trend of the molar selectivity [Ar]/[totC$_3$] and molar selectivity [Cum.]/[totC3] during the test in relation to the productivity of the catalyst.

The trend of the data indicated in FIG. 2 shows a very rapid deactivation of the catalyst unlike what is observed in the previous example.

In fact, the selectivities drop very rapidly and also the conversion of the isopropylic alcohol/propylene alkylating agent (not shown in the figure) drops to about 40% after reaching a productivity equal to only 50 Kg cumene/Kg beta.

From the data indicated in FIG. 2, the extreme importance of the water present in the liquid phase in determining the deactivation rate of the catalyst, is therefore evident.

Basically, when the concentration of water present in the liquid fraction existing in the reaction system remains within the limits established—regardless of the total water content present in the reaction system—there are no problems relating to rapid deactivation of the catalyst, whereas exceeding these limits corresponds to a more or less rapid deactivation of the catalyst.

It can also be observed that the reaction conditions adopted in this example are amply included in the range of normal reaction conditions for an industrial alkylation process of benzene (except for the WHSV) with propylene alone in liquid phase and that these conditions cannot therefore be applied when the alkylating agent also comprises isopropanol in total or partial substitution of propylene.

EXAMPLE 3

An alkylation test of benzene with a mixture of isopropylic alcohol and propylene is carried out using the same apparatus as that described in example 1. The catalyst used and the quantity charged into the reactor are the same as those specified in example 1.

The reaction conditions during the test are the following:

| | |
|---|---|
| Temperature at the inlet = | 180° C. |
| Pressure = | 30 barg |
| WHSV = | 20 h$^{-1}$ |
| [Benzene]/[C$_3$— + IPA] = | 7 moles/moles |
| [Propylene]/[IPA] = | 9 moles/moles |

The reaction conditions selected correspond to operating in completely liquid phase with a total concentration of water present equal to about 3050 ppm by weight.

This attribution is effected as already described in the previous examples, by assimilating the reaction system, as far as the compositions are concerned, to the system [benzene]/[propylene]=7 moles/moles and [benzene]/[water]=70.

Figure 3:
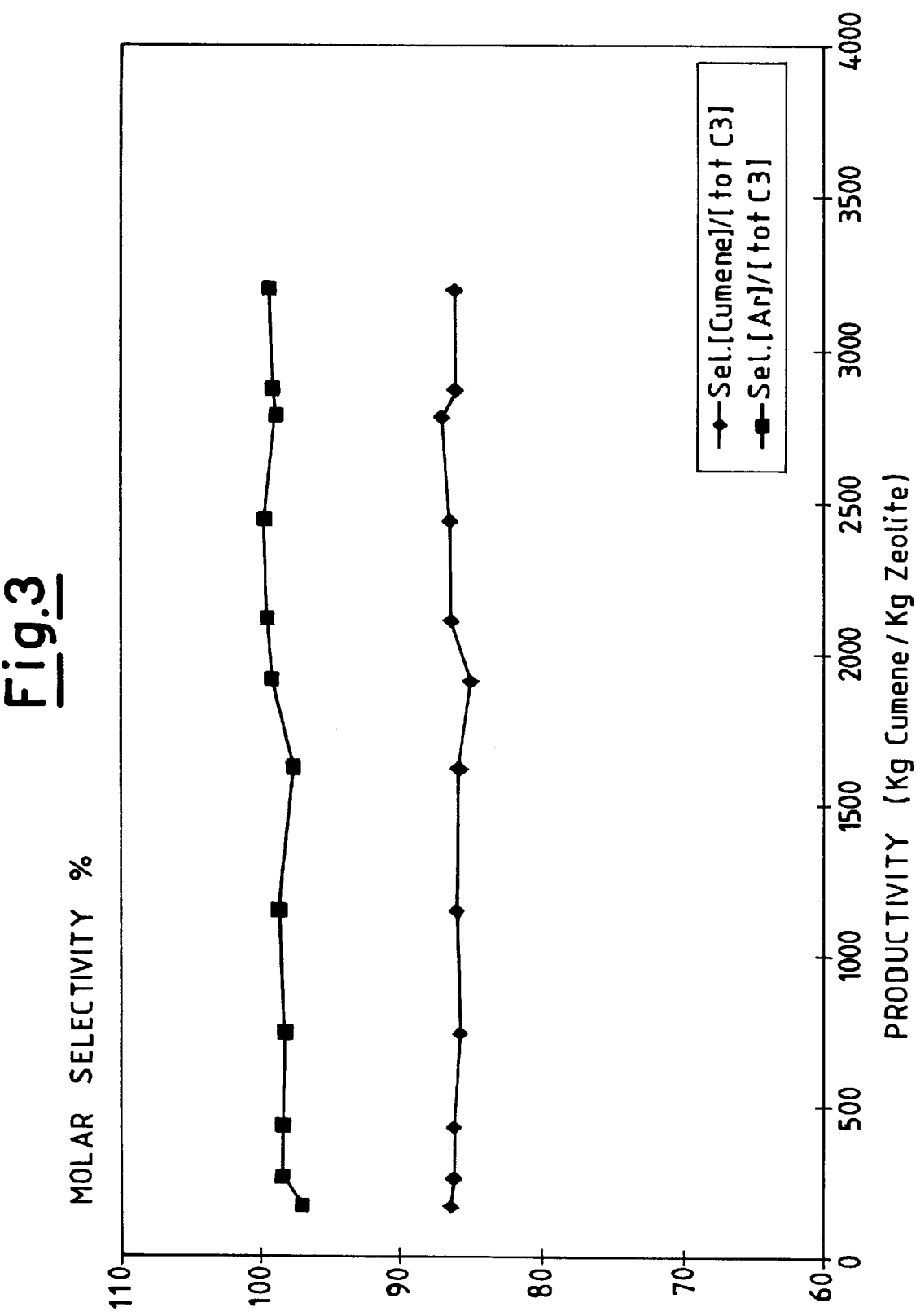

FIG. 3 shows the trend of the molar selectivity [Ar]/[totC$_3$] and molar selectivity [Cum.]/[totC$_3$] in relation to the productivity of the catalyst.

For the whole duration of the test, there were no signs of deactivation of the catalyst such as, for example, a drop in the conversion of isopropylic alcohol and/or propylene (quantitative for the whole duration of the test) or an increase in the fraction of polyalkylated products.

The selectivities during the whole test remained substantially unaltered with average values equal to about 86.0% for the selectivity[Cum]/[totC$_3$] and about 98.6% for the selectivity [Ar]/[totC$_3$].

It is evident that the different trend of the test with respect to the previous test can be attributed to the concentration of water present in the liquid phase which in this case is kept within the limits claimed herein unlike the previous example.

Example 4 (Comparative)

An alkylation test of benzene is carried out with isopropylic alcohol using the experimental equipment described below.

The experimental equipment consists of tanks for the benzene and isopropylic alcohol reagents, feeding pumps of the reagents to the reactor, pre-heating unit of the reagents, steel reactor situated inside an electric heating oven, regulation loop of the temperature inside the reactor, regulation loop of the pressure inside the reactor, reactor effluent cooler and collection system of the liquid and gaseous products.

In particular, the reactor consists of a cylindrical steel tube with a mechanical sealing system and a diameter equal to about 2 cm. A thermometric holder having a diameter of 1 mm is situated along the major axis of the reactor, inside which there is a thermocouple free to run along the major axis of the reactor.

A catalyst based on beta zeolite, prepared according to the procedure described in patent application EP 847,802 in example 4, is charged into the reactor in a quantity corresponding to a height of the catalytic bed equal to 10 cm. A quantity of inert material is charged on top of and below the catalytic bed to complete the bed. The benzene and isopropanol (IPA) reagents—preheated and premixed in a suitable mixer—are fed to the reactor with up flow.

The analysis of the reaction products is carried out as described in example 1. The reaction conditions during the test are the following:

| | |
|---|---|
| Reaction temperature = | 190° C. |
| Reaction pressure = | 19 barg |
| WHSV: | 4 h$^{-1}$ |
| [Benzene]/[IPA] = | 5.82 moles/moles |

The reaction conditions selected correspond to operating in mixed gas/liquid phase with a total concentration of water equal to about 35,000 ppm and a concentration of water present in the liquid phase equal to about 8,900 ppm.

This attribution is effected as already described in the previous examples, by assimilating the reaction system, as far as the compositions are concerned, to the system [benzene]/[propylene]=5.8 moles/moles and [benzene]/[water]=5.8.

Figure 4:
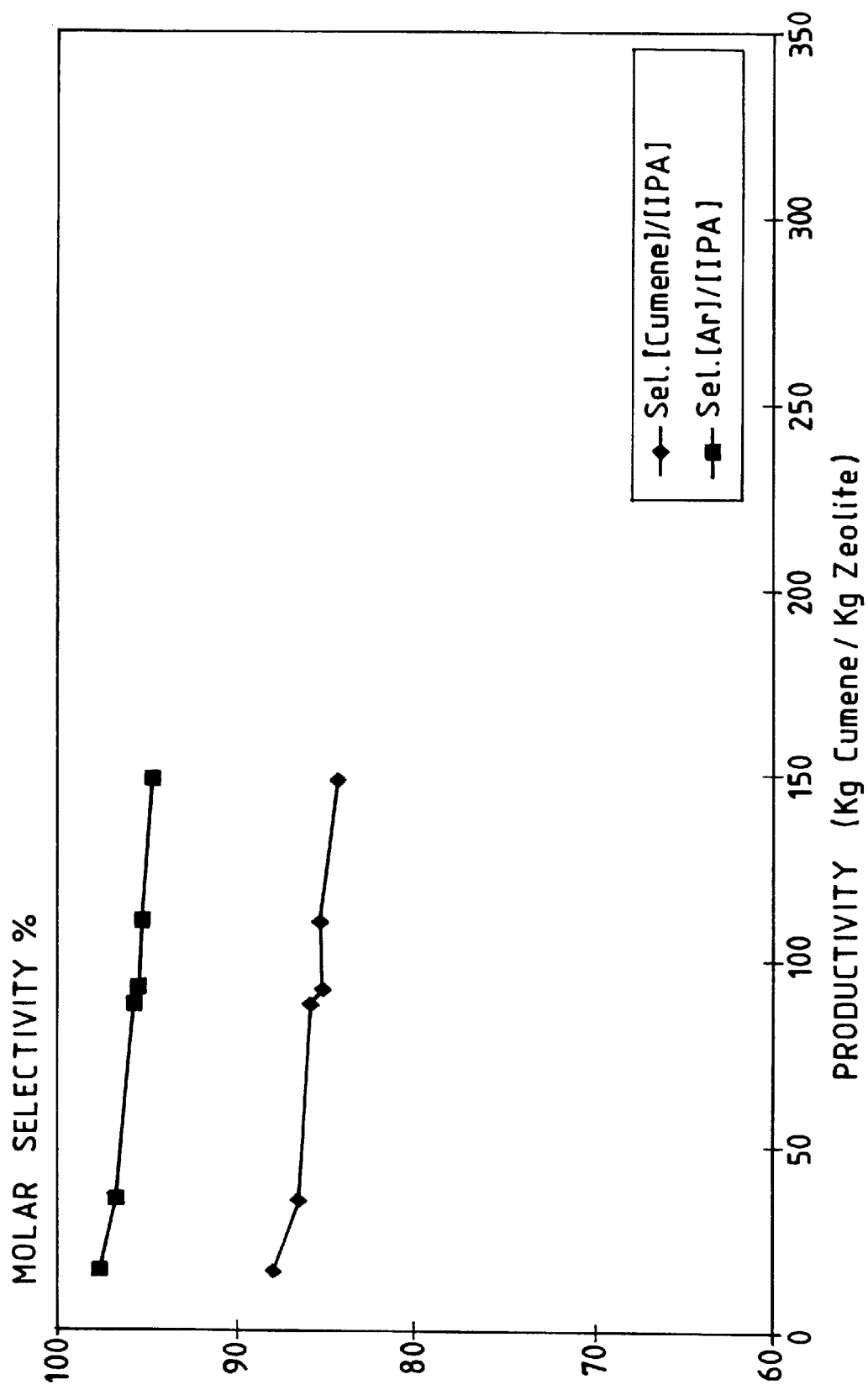

FIG. 4 shows the trend of the molar selectivity [Ar]/[IPA] and molar selectivity [Cum.]/[IPA] in relation to the productivity of the catalyst reached.

The trend of the data indicated in FIG. 4 shows a slow but constant deactivation of the catalyst unlike what is indicated in examples 1 and 3.

The type of deactivation however is different from that of the rapid deactivation observed in the test of example 2.

The selectivities show a certain decrease already with a productivity equal to 40 Kg cumene/Kg beta; together with these productivity values a slight drop in the conversion of the alcohol is also registered, which passes from quantitative to 99.7%.

The drop in selectivity and conversion in this test is however much slower than that described in example 2 and consequently the deactivation rate is slower in this test with respect to that registered in example 2.

It can therefore be concluded that the reaction conditions adopted in this test, corresponding to operating in mixed phase with a concentration of water present in the liquid phase equal to about 8,900 ppm, cause a gradual but not rapid deactivation of the catalyst, unlike the rapid deactivation observed in example 2.

EXAMPLE 5

An alkylation test of benzene with a mixture of isopropylic alcohol and propylene is carried out using the equipment described in example 1.

The catalyst used and the quantity charged into the reactor are the same as those specified in example 1. The reaction conditions during the test are as follows:

| | |
|---|---|
| Temperature at the inlet = | 180° C. |
| Pressure = | 19 barg |
| WHSV = | 20 h$^{-1}$ |
| [Benzene]/[Propylene + IPA] = | 7 moles/moles |
| [Propylene]/[IPA] = | 2.0 moles/moles |

The reaction conditions selected correspond to operating in mixed gas/liquid phase with a total concentration of water present equal to about 10,000 ppm and a concentration of water present in the liquid phase equal to about 6,400 ppm.

This attribution is effected as already described in the previous examples, by assimilating the reaction system, as far as the compositions are concerned, to that described in example 1.

Figure 5:
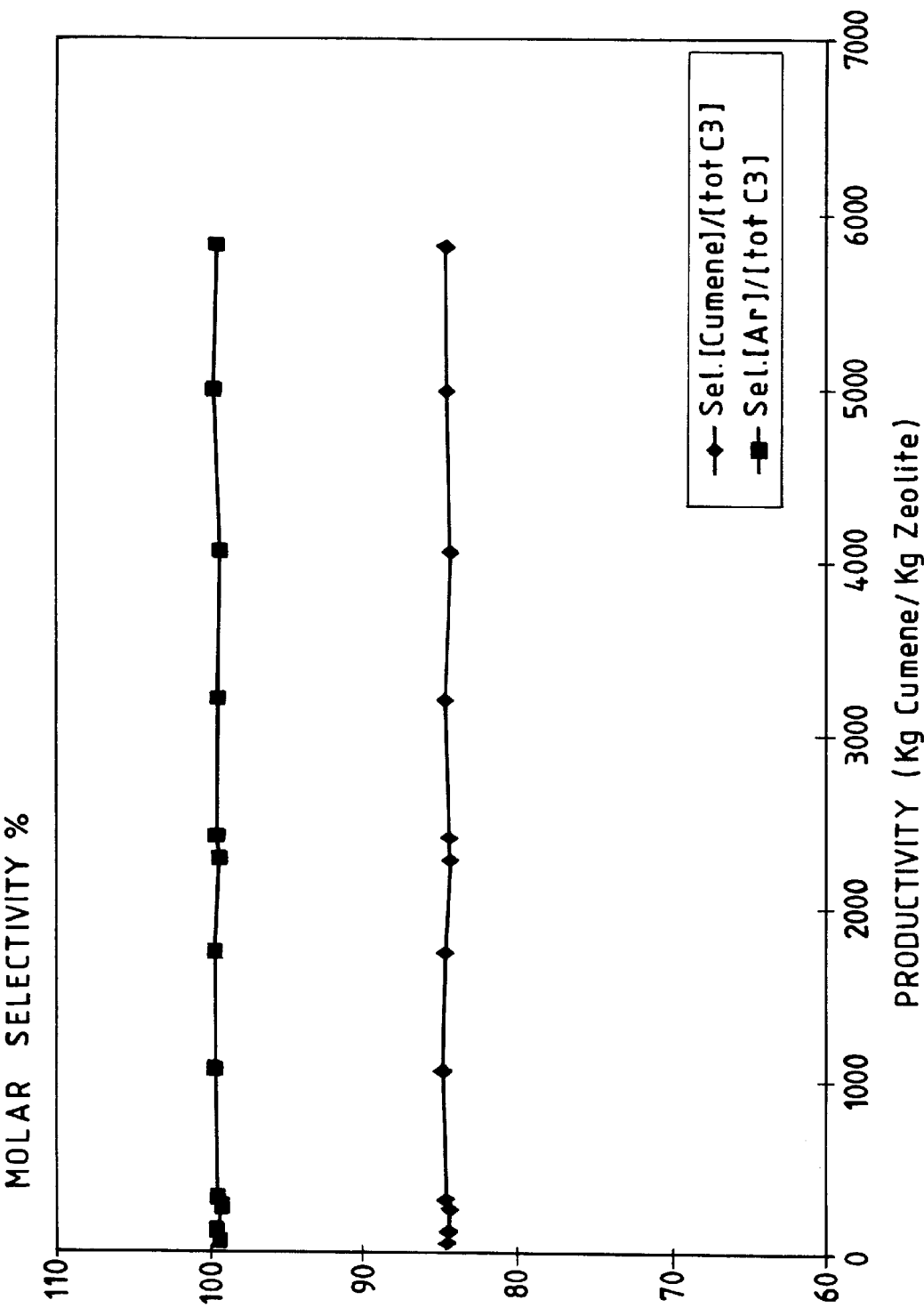

FIG. 5 shows the trend of the molar selectivity [Ar]/[totC$_3$] and molar selectivity [Cum.]/[totC$_3$] in relation to the productivity of the catalyst reached.

For the whole duration of the test, there were no signs of deactivation of the catalyst such as, for example, a drop in the conversion of alcohol and/or propylene (quantitative for the whole duration of the test) or an increase in the fraction of polyalkylated products.

The selectivities during the whole test remained substantially unaltered with values equal to about 85.3% for Sel. [Cum]/[totC$_3$] and about 96.0% for Sel.[Ar]/[totC$_3$].

In this case the concentration of water present in the liquid phase is within the limits indicated herein to avoid the rapid deactivation observed in example 2 or the slow but gradual deactivation of example 4.

Example 6 (Comparative)

The same experimental equipment described in example 4 is used and also the same catalyst, the analysis of the reaction products is carried out according to the procedure already described in example 1. The reaction conditions during the test are as follows:

| | |
|---|---|
| Reaction temperature = | 190° C. |
| Reaction pressure = | 30 bar |
| WHSV = | 4 h$^{-1}$ |
| [Benzene]/[IPA] in feeding = | 5.82 moles/moles |

These conditions ensure that the reaction system is completely in liquid phase.

More specifically, the reaction conditions selected correspond to operating in the presence of liquid phase alone with a total concentration of water present equal to about 35,000 ppm.

This attribution is effected as already described in the previous examples, by assimilating the reaction system, as far as the compositions are concerned, to the system [benzene]/[propylene]=5.8 moles/moles and [benzene]/[water]=5.8.

This attribution is effected as already described in example 4, obviously taking the different operating pressure into account.

Figure 6:
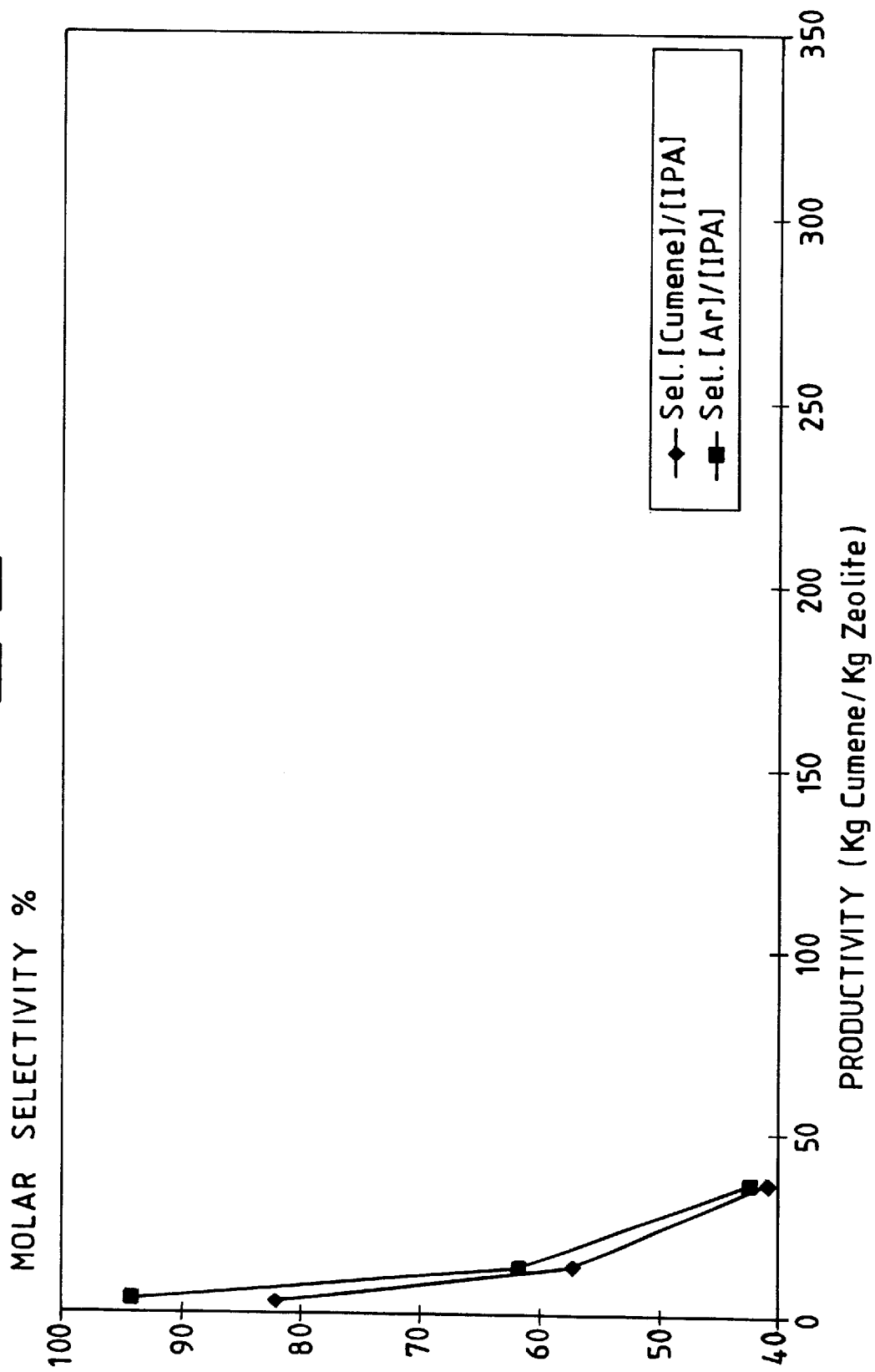

FIG. 6 shows the trend of the molar selectivity [Ar]/[IPA] and molar selectivity [Cum.]/[IPA] in relation to the productivity of the catalyst.

The trend of the data indicated in FIG. 6 shows an extremely rapid deactivation of the catalyst, unlike what is observed in example 4 where the deactivation was much slower and more gradual.

The selectivities drop very rapidly and also the conversion of isopropylic alcohol (not indicated in the figure) drops to about 80% after reaching productivities of less than 40 Kg of cumene/Kg beta.

It can therefore be observed that the reaction conditions adopted in this test, corresponding to operating in completely liquid phase with a concentration of water present in said phase equal to about 35,000 ppm, cause a rapid deactivation of the catalyst unlike what is indicated in examples 1, 3 and 5 and in particular example 4, carried out under completely analogous reaction conditions except for the reaction pressure.

A comparison with the data of example 4 demonstrates the actual importance of the water concentration limit claimed herein. On exceeding the limit of 8,000 ppm, the deactivation of the catalyst seems in fact gradual at first, as illustrated by the data of FIG. 4, and with an increase in the water content the deactivation becomes rapid, or extremely rapid, as can be seen from the data of FIG. 6 or FIG. 2.

EXAMPLE 7

An alkylation test of benzene with a mixture of isopropylic alcohol and propylene is carried out using the same equipment described in example 1, except for the introduction of an additional section which allows the reaction effluent to be recycled to the reactor itself.

In this test, the products leaving the reactor enter an AISI316 barrel having a volume of 2 liters, maintained at a pressure of 2.5 barg. The effluent, on cooling to room temperature, separates water which is continuously drained from the bottom of the barrel. Part of the organic phase, saturated with water and containing about 500 ppm, is recycled to the reaction section by means of a special dosage pump.

The part of organic phase not re-fed to the reaction section is sent instead to the product collection section and analyzed as is customary for the evaluation of the catalytic performance.

The ratio between the hourly quantity of effluent from the reaction section re-fed to the reaction section itself and the hourly quantity of effluent from the reaction section not re-fed to the reaction section is defined as the recycling ratio.

The reaction conditions during the test are as follows:

| | |
|---|---|
| Temperature at the inlet = | 180° C. |
| Pressure = | 30 barg |
| WHSV = | 20 h$^{-1}$ |
| [Benzene]/[Propylene + IPA]* = | 7.0 moles/moles |
| [Propylene]/[IPA]* = | 2.0 moles/moles |
| Recycling ratio = | 3 w/w |

*= ratios referring to the feeding of the fresh reagents to the reaction section These conditions ensure that the reaction system is completely in liquid phase.

More specifically, the reaction conditions selected correspond to operating in the presence of liquid phase alone with a total concentration of water present in the reactor equal to about 2,900 ppm, which without the recycling of the reactor effluent would instead be equal to about 10,000 ppm. i.e. equal to the total water developed in the reaction analogously to example 2. This attribution is effected as already described in the previous examples.

A catalyst based on beta zeolite, prepared according to the procedure described in patent application EP 847,802 in example 4, is charged into the reactor in a quantity corresponding to a height of the catalytic bed equal to 42.5 cm.

Figure 7:
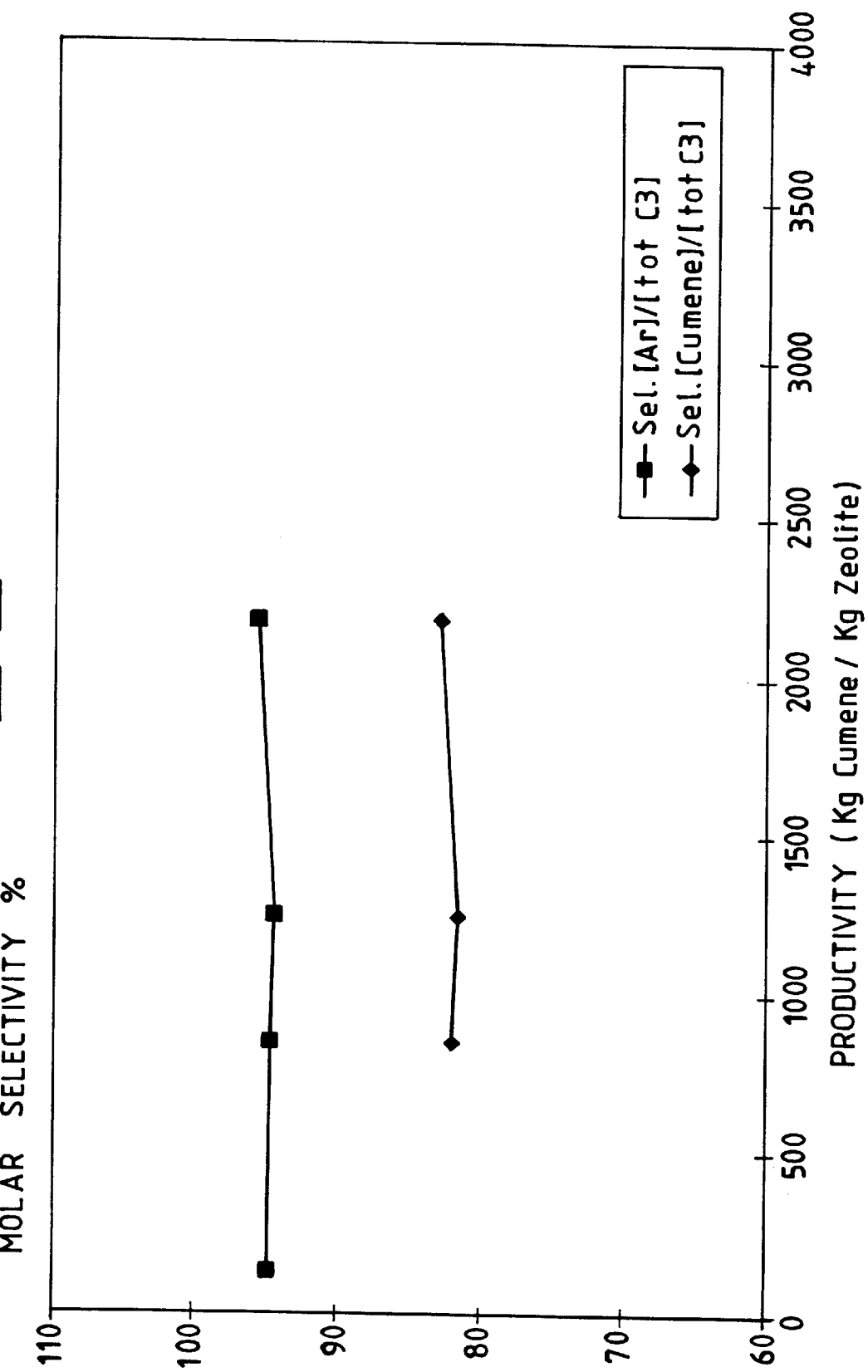

FIG. 7 shows the trend of the molar selectivity [Ar]/[totC$_3$] and molar selectivity [Cum.]/[totC$_3$] in relation to the productivity of the catalyst.

For the whole duration of the test, there were no signs of deactivation of the catalyst such as, for example, a drop in the conversion of alcohol and/or propylene (quantitative for the whole duration of the test) or an increase in the fraction of polyalkylated products.

The selectivities during the whole test remained substantially unaltered with values equal to about 82.1% for Sel. [Cum]/[totC$_3$] and about 94.8% for Sel.[Ar]/[totC$_3$].

The data and graph provided demonstrate that on diluting the content of water produced by the dehydration of isopropylic alcohol by recycling part of the reactor effluent to the reactor itself, it is possible to avoid the problem of the catalyst deactivation which would, on the other hand, take place without the recycling and with the same other operating conditions, due to the high concentration of water.

The expedient of recycling the reaction effluent to the reactor therefore proves to be an adequate system for keeping the concentration of water present within the limits claimed herein in order to avoid problems relating to the rapid deactivation of the catalyst which, however, arise when operating outside these limits.

Example 8 (Comparative)

An alkylation test of benzene with a mixture of isopropylic alcohol and propylene is carried out using the equipment described in example 1.

The reaction conditions during the test are as follows:

| | |
|---|---|
| Temperature at the inlet = | 180° C. |
| Pressure = | 14 barg |
| WHSV = | 20 h$^{-1}$ |
| [Benzene]/[Propylene + IPA] = | 7 moles/moles |
| [Propylene]/[IPA] = | 2.0 moles/moles |

The reaction conditions selected correspond to operating in mixed gas/liquid phase with a total concentration of water present equal to about 10,000 ppm and a concentration of water present in the liquid phase equal to about 3,180 ppm.

This attribution is effected as already described in the previous examples, by assimilating the reaction system, as far as the compositions are concerned, to that described in example 1.

A commercial catalyst TSZ 330 HUD (based on Y zeolite) is charged into the reactor in a quantity corresponding to a catalytic bed height equal to 42.5 cm.

Figure 8:
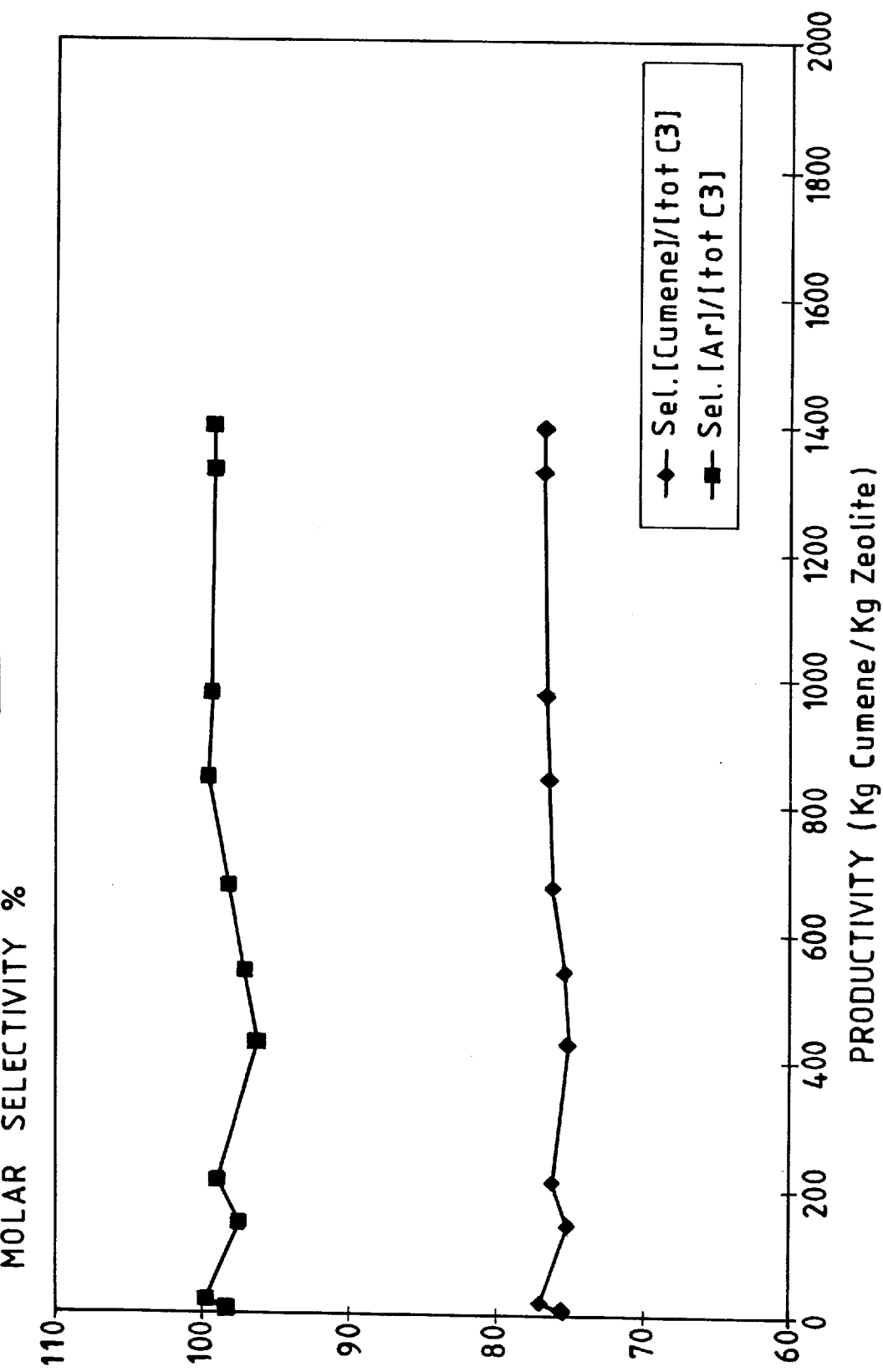

FIG. 8 shows the trend of the molar selectivity [Ar]/[totC$_3$] and molar selectivity [Cum.]/[totC$_3$] in relation to the productivity of the catalyst.

The data indicated in the graph of FIG. 8 clearly demonstrate, if compared with those of FIG. 1 relating to the experiment described in example 1, that against quite a similar [Ar.]/[totC$_3$] selectivity, there is a much lower [Cum.]/[totC$_3$] selectivity with the TSZ 330 HUD catalyst, based on Y zeolite, with respect to the catalyst based on beta zeolite.

The [Ar.]/[totC$_3$] selectivity, in fact, in this test has an average value equal to 98.5% against an average value equal to about 98.8% in example 1 but the [Cum.]/[totC$_3$] selectivity on the other hand has an average value equal to about 76.1% against an average value equal to about 84.0% in example 1.

This means that the fraction of polyalkylated products, especially diisopropylbenzenes, is much greater with the TSZ 330 HUD catalyst than the fraction of polyalkylated products which is formed with the catalyst used in example 1 based on beta zeolite.

In an industrial process for the production of Cumene which comprises the recovery of this fraction in a separate transalkylation section with benzene to give cumene this obviously represents a disadvantage with respect to an analogous process which uses the catalyst based on beta zeolite used in example 1.

From the point of view of the catalyst deactivation, a substantially constant trend of the selectivity can be noted on the other hand, which indicates the absence of the rapid and/or gradual deactivation phenomena observed in some of the previous examples.

This means that also with a different catalyst from that used in example 1, with completely different catalytic performances in terms of selectivity, there is still the positive effect of the operating conditions claimed herein which guarantee absence of deactivation of the catalyst in the reaction in question, regardless of the total content of water present in the reaction mixture.

The water concentration limit claimed herein therefore allows the alkylation reaction of benzene with isopropanol or mixtures of isopropanol/propylene to be carried out regardless of the total water content in the reaction—and therefore total content of isopropylic alcohol in the feeding—and regardless of the zeolitic catalyst used.

What is claimed is:

1. A process comprising alkylation of an aromatic compound by reaction of the aromatic compound with isopropanol, alone or mixed with propylene, in the presence of a catalytic composition comprising a zeolite, under mixed gas-liquid phase conditions or under completely liquid phase conditions, at such temperature and pressures that the concentration of water in the reaction liquid phase is not higher than 8,000 ppm, regardless of the total water content present in the reaction mixture.

2. The process according to claim 1, wherein the aromatic compound is benzene.

3. The process according to claim 2, wherein the concentration of water in the liquid phase is less than 7,000 ppm.

4. The process according to claim 3, wherein the zeolite is selected from the group consisting of beta, Y, ZSM-12 and mordenite.

5. The process according to claim 3, wherein the zeolite is a porous crystalline material having the composition:

wherein
  n is the oxidation state of M,
  x is less than 1,
  y ranges from 5 to 100,
  w is from 0 to 4,
  M is a metal selected from groups IA, IIA, and IIIA of the Periodic System, and transition metals, and
  TEA is tetraethylammonium.

6. The process according to claim 3, wherein the reaction is carried out in the presence of a catalytic composition comprising a beta zeolite and an inorganic ligand.

7. The process according to claim 2, wherein the zeolite is a porous crystalline material having the composition:

wherein
n is the oxidation state of M,
x is less than 1,
y ranges from 5 to 100,
w is from 0 to 4,
M is a metal selected from groups IA, IIA, and IIIA of the Periodic System, and transition metals, and
TEA is tetraethylammonium.

8. The process according to claim 7, wherein the porous crystalline material is present in acid form.

9. The process according to claim 2, wherein the reaction is carried out in the presence of a catalytic composition comprising a beta zeolite and an inorganic ligand.

10. The process according to claim 9, characterized by an extra-zeolite porosity comprising, for a fraction of at least 25%, pores with a radius higher than 100 Å, or further characterized by a total extra-zeolitic pore volume equal to or greater than 0.80 ml/g.

11. The process according to claim 10, wherein the inorganic ligand is selected from the group consisting of oxides of silicon, aluminum, zirconium and magnesium.

12. The process according to claim 9, wherein the inorganic ligand is selected from the group consisting of oxides of silicon, aluminum, zirconium and magnesium.

13. The process according to claim 2, wherein the reaction is carried out with isopropanol alone.

14. The process according to claim 13, wherein the reaction is carried out with a molar ratio between benzene and isopropanol ranging from 3 to 10.

15. The process according to claim 14, wherein the reaction is carried out with a molar ratio between benzene and isopropanol ranging from 4 to 8.

16. The process according to claim 2, wherein the reaction is carried out with an alkylating mixture consisting of isopropanol and propylene.

17. The process according to claim 16, wherein the reaction is carried out with a molar ratio between benzene and alkylating mixture ranging from 3 to 10.

18. The process according to claim 17, wherein the reaction is carried out with a molar ratio between benzene and alkylating mixture ranging from 4 to 8.

19. The process according to claim 18, wherein the reaction is carried out using an alkylating mixture consisting of isopropanol and propylene in a molar ratio ranging from 10 to 0.01.

20. The process according to claim 19, wherein the reaction is carried out using an alkylating mixture consisting of isopropanol and propylene in a molar ratio ranging from 5 to 0.1.

21. The process according to claim 17, wherein the reaction is carried out using an alkylating mixture consisting of isopropanol and propylene in a molar ratio ranging from 10 to 0.01.

22. The process according to claim 21, wherein the reaction is carried out using an alkylating mixture consisting of isopropanol and propylene in a molar ratio ranging from 5 to 0.1.

23. The process according to claim 16, wherein the reaction is carried out using an alkylating mixture consisting of isopropanol and propylene in a molar ratio ranging from 10 to 0.01.

24. The process according to claim 23, wherein the reaction is carried out using an alkylating mixture consisting of isopropanol and propylene in a molar ratio ranging from 5 to 0.1.

25. A process for the preparation of phenol comprising the preliminary alkylation of benzene with isopropanol, alone or mixed with propylene, the oxidation of the cumene thus obtained, the acid treatment of cumylhydroperoxide, the hydrogenation of the acetone which is formed as by-product and recycling of the isopropanol which is thus formed, wherein the initial alkylation of the benzene takes place according to the process of claim 2.

26. The process according to claim 2, wherein polyalkylated products present in effluents of the reaction are separated in a specific fractionation section and sent to a transalkylation section with benzene.

27. The process according to claim 2, wherein the reaction is carried out in a reaction zone, and effluent from the reaction zone, after cooling in a cooling section, is separated in a separation section into an organic phase and an aqueous phase, after which the aqueous phase is discharged, whereas the organic phase is sent to a fractionation section, or partly re-fed to the reaction zone.

28. The process, according to claim 27, wherein the reaction zone comprises two or more reactors, in at least one of which the alkylation is carried out with isopropanol or a mixture of isopropanol and propylene and in at least one of which the alkylation is carried out with propylene alone.

29. The process according to claim 28, wherein the fractionation section comprises a depropanating zone for the separation of propane present in an olefinic charge for alkylation, a debenzenating zone, a cumene finishing zone and a zone for the separation of diisopropylbenzenes, and wherein the depropanating zone comprises a first depropanating column to which the organic phase downstream of the cooling and separation sections is fed together with a recycled benzene stream, and also a second depropanating column to which a stream rich in benzene at the head of the first depropanating column, is fed, and two streams leave the bottom of said depropanating columns, which are sent to the debenzenating column.

30. The process according to claim 29, wherein separation of the aqueous phase from the organic phase is carried out in reflux accumulators of the depropanating columns.

31. The process according to claim 27, wherein the fractionation section comprises a depropanating zone for the separation of propane present in an olefinic charge for alkylation, a debenzenating zone, a cumene finishing zone and a zone for the separation of diisopropylbenzenes, and wherein the depropanating zone comprises a first depropanating column to which the organic phase downstream of the cooling and separation sections is fed together with a recycled benzene stream, and also a second depropanating column to which a stream rich in benzene at the head of the first depropanating column, is fed, and two streams leave the bottom of said depropanating columns, which are sent to the debenzenating column.

32. The process according to claim 31, wherein separation of the aqueous phase from the organic phase is carried out in reflux accumulators of the depropanating columns.

33. The process according to claim 27, wherein the fractionation section comprises a depropanating zone, wherein the depropanating zone comprises two depropanating columns, the first of which is fed with effluents leaving an alkylation section in which the alkylation is carried out with isopropanol, alone or with propylene, the second of which is fed with effluents leaving an alkylation section in which the alkylation is carried out with propylene alone.

34. The process according to claim 33, wherein separation of the aqueous phase from the organic phase is carried out in reflux accumulators of the depropanating columns.

35. The process according to claim 27, wherein the fractionation section comprises a depropanating zone, wherein the depropanating zone comprises two depropanating columns, the first of which is fed with effluents leaving an alkylation section in which the alkylation is carried out with isopropanol, alone or with propylene, the second of which is fed with effluents leaving an alkylation section in which the alkylation is carried out with propylene alone.

36. The process according to claim 30, wherein separation of the aqueous phase from the organic phase is carried out in reflux accumulators of the depropanating columns.

37. The process according to claim 2, wherein the zeolite is selected from the group consisting of beta, Y, ZSM-12 and mordenite.

38. The process according to claim 2, wherein the reaction is carried out at a temperature ranging from 170° C. to 230° C., at a pressure ranging from 10 to 50 bars and at a WHSV ranging from 10 $h^{-1}$ to 1 $h^{-1}$.

39. The process according to claim 2, wherein the reaction produces a reaction effluent comprising an organic phase and an aqueous phase, and wherein part of the organic phase of the reaction effluent is re-fed to the reaction, after cooling and separation of the aqueous phase and organic phase.

40. The process according to claim 1, wherein the zeolite is selected from the group consisting of beta, Y, ZSM-12 and mordenite.

41. The process according to claim 1, wherein the reaction is carried out with isopropanol alone.

42. The process according to claim 1, wherein the reaction is carried out at a temperature ranging from 170° C. to 230° C., at a pressure ranging from 10 to 50 bars and at a WHSV ranging from 10 $h^{-1}$ to 1 $h^{-1}$.

43. The process according to claim 1, wherein the reaction is carried out with an alkylating mixture consisting of isopropanol and propylene.

44. The process according to claim 43, wherein the reaction is carried out using an alkylating mixture consisting of isopropanol and propylene in a molar ratio ranging from 10 to 0.01.

45. The process according to claim 44, wherein the reaction is carried out using an alkylating mixture consisting of isopropanol and propylene in a molar ratio ranging from 5 to 0.1.

46. The process according to claim 1, wherein the reaction produces a reaction effluent comprising an organic phase and an aqueous phase, and wherein part of the organic phase of the reaction effluent is re-fed to the reaction, after cooling and separation of the aqueous phase and organic phase.

47. A process comprising alkylation of an aromatic compound by reaction of the aromatic compound with isopropanol, alone or mixed with propylene, in the presence of a catalytic composition comprising a zeolite, under mixed gas-liquid phase conditions or under completely liquid phase conditions, at such temperature and pressures that the concentration of water in the reaction liquid phase is not higher than 8,000 ppm, regardless of the total water content present in the reaction mixture, wherein the zeolite is a porous crystalline material having the composition:

$$[(x/n)M(1\pm0.1-x)TEA]AlO_2.ySiO_2.wH_2O$$

wherein n is the oxidation state of M, x is less than 1, y ranges from 5 to 100, w is from 0 to 4, M is a metal selected from groups IA, IIA, and IIIA of the Periodic System, and transition metals, and TEA is tetraethylammonium.

* * * * *